(12) United States Patent
Jenson

(10) Patent No.: US 8,556,966 B2
(45) Date of Patent: Oct. 15, 2013

(54) ANNULOPLASTY DEVICE

(75) Inventor: Mark L. Jenson, Greenfield, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 187 days.

(21) Appl. No.: 13/070,059

(22) Filed: Mar. 23, 2011

(65) Prior Publication Data

US 2011/0238169 A1 Sep. 29, 2011

Related U.S. Application Data

(60) Provisional application No. 61/316,475, filed on Mar. 23, 2010.

(51) Int. Cl.
*A61F 2/24* (2006.01)

(52) U.S. Cl.
USPC ........................................ 623/2.36

(58) Field of Classification Search
USPC ................................ 623/2.36–2.38
See application file for complete search history.

(56) References Cited

U.S. PATENT DOCUMENTS

| | | | |
|---|---|---|---|
| 4,917,698 A * | 4/1990 | Carpentier et al. | 623/2.36 |
| 5,104,407 A * | 4/1992 | Lam et al. | 623/2.36 |
| 5,720,746 A | 2/1998 | Soubeiran | |
| 5,980,570 A * | 11/1999 | Simpson | 623/2.11 |
| 6,348,068 B1 * | 2/2002 | Campbell et al. | 623/2.36 |
| 6,709,456 B2 | 3/2004 | Langberg et al. | |
| 6,726,716 B2 * | 4/2004 | Marquez | 623/2.36 |
| 6,974,476 B2 * | 12/2005 | McGuckin et al. | 623/2.36 |
| 7,294,148 B2 | 11/2007 | McCarthy | |
| 2003/0191528 A1 * | 10/2003 | Quijano et al. | 623/2.37 |
| 2003/0208264 A1 * | 11/2003 | McCarthy et al. | 623/2.11 |
| 2004/0088047 A1 * | 5/2004 | Spence et al. | 623/2.36 |
| 2004/0092858 A1 * | 5/2004 | Wilson et al. | 604/9 |
| 2004/0254600 A1 | 12/2004 | Zarbatany | |
| 2005/0043791 A1 * | 2/2005 | McCarthy et al. | 623/2.36 |
| 2005/0131533 A1 * | 6/2005 | Alfieri et al. | 623/2.36 |
| 2005/0177228 A1 | 8/2005 | Solem | |
| 2006/0276891 A1 | 12/2006 | Nieminen et al. | |
| 2007/0118215 A1 | 5/2007 | Moaddeb | |
| 2007/0288090 A1 * | 12/2007 | Solem et al. | 623/2.37 |
| 2008/0208331 A1 * | 8/2008 | McCarthy et al. | 623/2.37 |
| 2008/0293996 A1 * | 11/2008 | Evans et al. | 600/16 |
| 2009/0043382 A1 * | 2/2009 | Maurer et al. | 623/2.36 |
| 2009/0287303 A1 * | 11/2009 | Carpentier | 623/2.36 |
| 2010/0016891 A1 * | 1/2010 | Kennedy et al. | 606/228 |
| 2011/0178362 A1 * | 7/2011 | Evans et al. | 600/16 |

(Continued)

FOREIGN PATENT DOCUMENTS

FR 2726757 5/1996

OTHER PUBLICATIONS

International Search Report corresponding to International Patent Application PCT/US2011/000528, mailing date Jun. 21, 2011.

*Primary Examiner* — Suzette J Gherbi

(74) *Attorney, Agent, or Firm* — Brooks, Cameron & Huebsch, PLLC

(57) ABSTRACT

Devices, systems, and methods associated with annuloplasty are described herein. One or more annuloplasty devices include a number of longitudinal filaments moveable between an introductory configuration and a deployed configuration, wherein the number of longitudinal filaments are one or more lengths, and a shell, wherein the shell contains the number of longitudinal filaments and a curable polymer to maintain the annuloplasty device in a deployed configuration.

13 Claims, 4 Drawing Sheets

(56) References Cited

U.S. PATENT DOCUMENTS

| | | | |
|---|---|---|---|
| 2011/0257741 A1* | 10/2011 | Moaddeb et al. | 623/2.37 |
| 2012/0029614 A1* | 2/2012 | Burnside et al. | 623/1.15 |
| 2012/0125527 A1* | 5/2012 | Kennedy et al. | 156/167 |
| 2012/0191183 A1* | 7/2012 | Rzany et al. | 623/2.17 |
| 2012/0296419 A1* | 11/2012 | Richardson et al. | 623/2.36 |

* cited by examiner

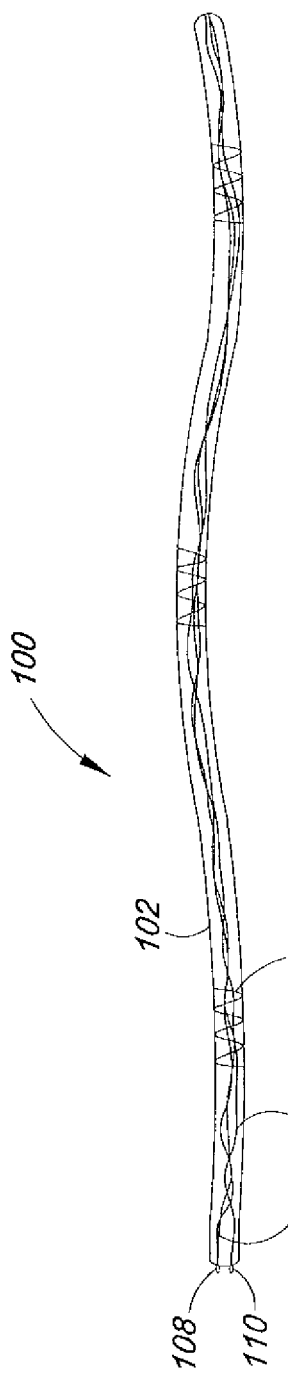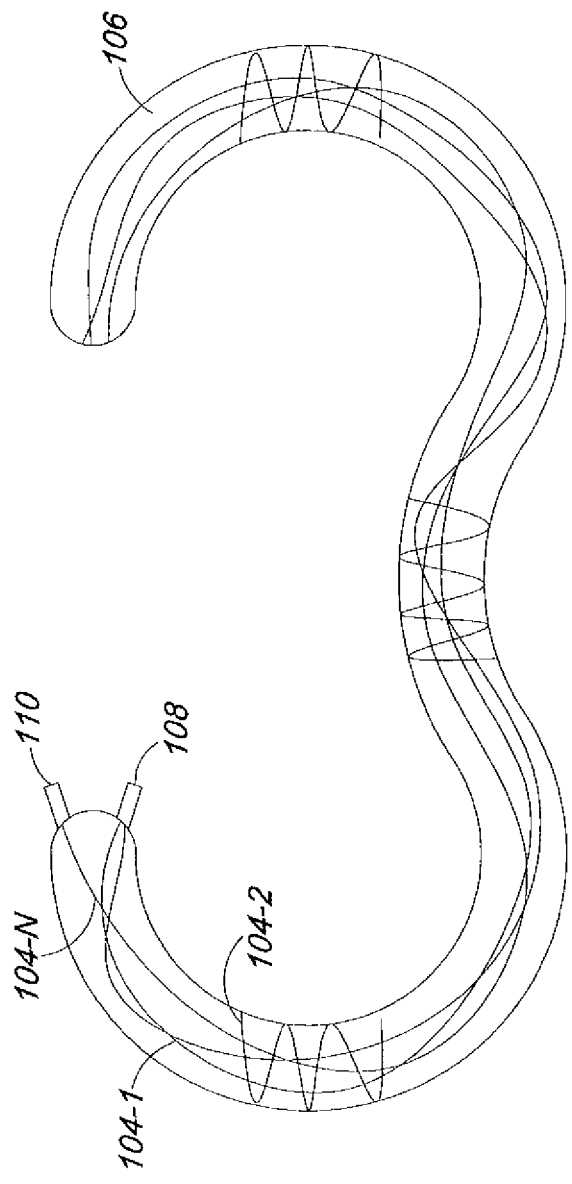
Fig. 1A
Fig. 1B

ANNULOPLASTY DEVICE

PRIORITY INFORMATION

This application claims priority to U.S. Provisional Application No. 61/316,475 filed on Mar. 23, 2010, the specification of which is incorporated herein by reference.

TECHNICAL FIELD

The present disclosure relates generally to annuloplasty devices, systems, and methods, and more particularly, to mitral annuloplasty devices, systems, and methods.

BACKGROUND

Mitral annuloplasty, by implantation of a shaped annuloplasty ring, can be used to repair the mitral valve for treating functional mitral regurgitation. Annuloplasty prostheses, e.g., annuloplasty rings or annuloplasty bands, can be used as part of valvular reconstructive surgery to assist in the correction of heart valve defects such as stenosis and valvular insufficiency. The mitral valve includes a valve annulus and valve leaflets. Mitral regurgitation is the back flow of blood from the left ventricle to the left atrium through the mitral valve. Dilation of the mitral valve annulus can prevent competence of the valve but also results in distortion of the normal shape of the valve orifice.

In annuloplasty procedures the annulus can be remodeled using surgical techniques on the mitral valve and/or prosthetic treatments for the mitral valve. It has been show through clinical trials that the repair of the valve, when technically possible, produces better long-term results as compared to valve replacement. Even when other repairs to the mitral valve are made, most of the time annuloplasty is performed.

Annuloplasty can be performed by open surgical procedure, but less invasive and percutaneous approaches can also be used. One goal in annuloplasty is to make the mitral annulus smaller, particularly in the septal-lateral dimension. A number shapes of rings can be used, such as rounded D shape, and can include various small curves, out-of-plane saddle shapes, complete rings, and incomplete rings, among others, depending on patient requirements and physician preference. Also, a suture-based cinching procedure can be used to perform an annular reshaping similar to the prosthetic procedures.

Many percutaneous annuloplasty approaches place a rigid structure in the coronary sinus, which is near the mitral annulus. These procedures that place a rigid structure in the coronary sinus may not be effective or safe in all patients due to the anatomy of the coronary sinus, the mitral annulus, and the nearby circumflex coronary artery. In particular, coronary sinus devices may not be as effective as devices placed at the mitral annulus. Also, crossing of the coronary sinus over the circumflex artery can cause dangerous compression of the artery by a rigid annuloplasty device placed in the coronary sinus. The annuloplasty device must be quite stiff to be effective which presents difficulties in safely placing the device near the mitral annulus using a less invasive, percutaneous procedure.

BRIEF DESCRIPTION OF THE DRAWINGS

FIG. 1A illustrates an annuloplasty device in an introductory configuration in accordance with one or more embodiments of the present disclosure.

FIG. 1B illustrates an annuloplasty device in a deployed configuration in accordance with one or more embodiments of the present disclosure.

DETAILED DESCRIPTION

Figure 2:
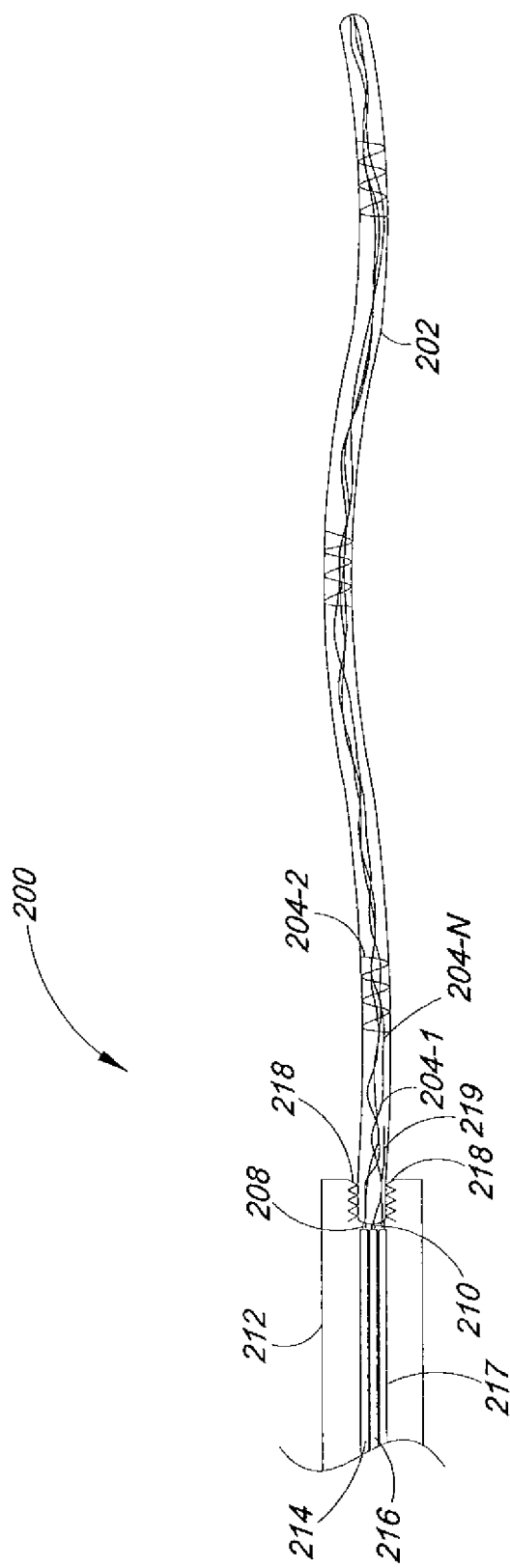
FIG. 2 illustrates an annuloplasty device delivery system in accordance with one or more embodiments of the present disclosure.

Devices, systems, and methods associated with annuloplasty are described herein. In one or more embodiment, an annuloplasty device includes a number of longitudinal filaments moveable between an introductory configuration and a deployed configuration, wherein the number of longitudinal filaments are one or more lengths, and a shell, wherein the shell contains the number of longitudinal filaments and a curable polymer to maintain the annuloplasty device in a deployed configuration.

In the following detailed description of the present disclosure, reference is made to the accompanying drawings that form a part hereof, and in which is shown by way of illustration how one or more embodiments of the disclosure may be practiced. These embodiments are described in sufficient detail to enable those of ordinary skill in the art to practice the embodiments of this disclosure, and it is to be understood that other embodiments may be utilized and that process, electrical, and/or structural changes may be made without departing from the scope of the present disclosure.

The figures herein follow a numbering convention in which the first digit or digits correspond to the drawing figure number and the remaining digits identify an element or component in the drawing. Similar elements or components between different figures may be identified by the use of similar digits. For example, 102 may reference element "02" in FIG. 1A, and a similar element may be referenced as 202 in FIG. 2. As will be appreciated, elements shown in the various embodiments herein can be added, exchanged, and/or eliminated so as to provide a number of additional embodiments of the present disclosure. In addition, the proportion and the relative scale of the elements provided in the figures are intended to illustrate various embodiments of the present invention and are not to be used in a limiting sense.

FIG. 1A illustrates an annuloplasty device 100 in an introductory configuration in accordance with one or more embodiments of the present disclosure. In FIG. 1A, annuloplasty device 100 includes a shell 102 and a number of filaments 104-1, 104-2, . . . , 104-N. Filaments 104-1, 104-2, . . . , 104-N can be of various lengths and can be coupled to shell 102. For example, filaments 104-1 and 104-N can have a length spanning the entire cavity of shell 102 and filament 104-2 can be shorter, only spanning a portion of the shell 102. Filaments can be coupled to the shell by surrounding an end of a filament with the shell material. Filaments 104-1, 104-2, . . . , 104-N can also be formed into a pattern using various methods, such as braiding, weaving, or coupling together. In FIG. 1A, filament 104-2 is part of a pattern formed at a location within the shell 102 of the annuloplasty device 100. The pattern that the filaments form can be helpful in transitioning the annuloplasty device from the introductory configuration to a deployed configuration and maintaining the annuloplasty device in the deployed configuration.

In one or more embodiments, filaments 104-1, 104-2, ..., 104-N can be made of metal, such as nitinol and stainless steel, among other metals. In some embodiments, filaments 104-1, 104-2, ..., 104-N can also be made of glass, ceramics, and polymers, among other materials. Filaments 104-1, 104-2, ..., 104-N can have a round and/or rectangular cross-section, among other cross-sectional shapes, and can be solid or tubular.

In one or more embodiments, a majority of the filaments, e.g. 104-1 and 104-N, can span the entire length of the cavity inside the shell 102. A number of shorter filaments, e.g., 104-2, can be provided at various locations in the annuloplasty device 100. These shorter filaments can provide added strength to the annuloplasty device and can be used to shape the annuloplasty device 100 in a desired position.

In one or more embodiments, the shell 102 can be made of a flexible material, such as a polymer, among other materials, that can bend, and also expand by unfolding and/or by elastic expansion when inflated. The flexible material of the shell can allow the annuloplasty device to be maneuvered through the vasculature while not harming the vasculature in the process of maneuvering the annuloplasty device through the vasculature to the heart.

In FIG. 1A, the annuloplasty device 100 is shown in an introductory configuration, e.g., a configuration prior to introduction and deployment within a patient. The introductory configuration is substantially longitudinal, such that the annuloplasty device can be inserted percutaneously into the body and moved towards the heart through the vasculature while in the introductory configuration. The annuloplasty device in an introductory configuration can be approximately 8 to 12 cm long and have an approximate diameter of 2 to 3 mm. Once the annuloplasty device is positioned proximate to the mitral annulus, the annuloplasty device is transformed to a deployed configuration, such as illustrated in FIG. 1B and discussed below.

FIG. 1B illustrates an annuloplasty device 100 in a deployed configuration in accordance with one or more embodiments of the present disclosure. In FIG. 1B, the annuloplasty device 100 is in a deployed configuration to be placed around and/or proximate to a mitral annulus. The annuloplasty device 100 can be shaped into the deployed configuration to be an approximate fit of the mitral annulus to partially encircle and provide support for the mitral annulus and provide for pinching the annulus to a smaller dimension. The annuloplasty device 100 can be shaped into the deployed configuration by inflating the shell 102 with a contrast medium and/or a polymer 106, e.g., a curable polymer. The contrast medium and/or the polymer 106 can be introduced into the shell 102 via a valve, e.g., 108 and 110. Valves 108, 110 can be coupled to a delivery device, e.g., delivery device 212 shown in FIG. 2, which can provide the contrast medium and/or polymer 106 from an outside source. The contrast medium and/or polymer 106 can cause the filaments 104-1, 104-2, ..., 104-N to take on their pre-shaped form which corresponds to the deployed configuration. The filaments 104-1, 104-2, ..., 104-N can be permanently maintained by hardening the polymer through a curing process, such as thermal exposure, ultraviolet light exposure, electrical exposure, and or a chemical reaction, among other curing processes. In one or more embodiments, the filaments 104-1, 104-2, ..., 104-N can be introduced to the shell 102 via valves 108 and 110 when deploying the annuloplasty device 100.

In one or more embodiments, strengthening additives, such as beads, fibers, and carbon nanotubes, among other strengthening additives, can be included in the polymer. The strengthening additives can provide additional support to the annuloplasty device and help the annuloplasty device maintain the deployed configuration.

In some embodiments, the annuloplasty device 100 can be transitioned from the introductory configuration to the deployed configuration using a shaping tool (not shown). The shaping tool can be inserted into the shell 102 via a lumen in the annuloplasty device 100. The shaping tool can shape the shell and the filaments into the desired shape of the deployed configuration. The shaping tool can be a shaped wire or stylet, one or more shaped stiffening rods, and/or an articulated structure that can bend into shape when desired, or a thermal-memory material that takes the required shape after placement, for example. A lumen can be provided in the annuloplasty device for insertion of the shaping tool. The shaping tool can be used to hold the annuloplasty device in a desired shape which compresses the mitral annulus to the desired circumference and/or septal-lateral dimension until the polymer is cured. A polymer can introduced into the shell of annuloplasty device 100 and cured to cause the annuloplasty device 100 to maintain the desired shape and the shaping tool can be removed from the shell of the annuloplasty device 100 before or after the polymer is introduced into the shell of the annuloplasty device. In one or more embodiments, a shaping tool can be applied to the exterior of the shell and be used to achieve a desired deployment configuration of the annuloplasty device 100.

In one or more embodiments, the annuloplasty device 100 in the deployed configuration can be place around the mitral annulus in the coronary venous vasculature via the coronary sinus. In some embodiments, the annuloplasty device 100 in the deployed configuration can be placed in the left atrium and coupled to the tissue around the mitral annulus with attachment mechanisms to provide support for the initial annulus. In some embodiments, the annuloplasty device 100 in the deployed configuration can be placed proximate to the mitral annulus epicardially and coupled to the tissue around the mitral annulus with attachment mechanisms to provide support for the mitral annulus. Attachment mechanisms on the outer surfaces of the shell can include sutures, barbs, and/or hooks, among other attachment mechanisms.

FIG. 2 illustrates an annuloplasty device delivery system in accordance with one or more embodiments of the present disclosure. FIG. 2 illustrates an embodiment configured for delivery of an annuloplasty device, e.g., device 100 shown in FIGS. 1A and 1B, to a desired location within a patient's body. The annuloplasty device delivery system in FIG. 2 includes a delivery device 212 coupled to an annuloplasty device 200 with a coupling mechanism 218. The annuloplasty device 200 includes a shell 202 and a number of filaments 204-1, 204-2, ..., 204-N. The coupling mechanism 218 can be a removable coupling mechanism, such as a screw, fusible link, moveable jaws, or a pressure-actuated release, among other coupling mechanisms. The annuloplasty device delivery system can include a catheter or other device which activates the curing of the curable polymer. Also, time at temperature can be used to cure the curable polymer.

In one or more embodiments, procedures using the delivery system in FIG. 2 can include an incision to gain access to the vasculature, e.g. via the femoral vein or jugular vein, among others. For example, a guide catheter (not shown) can be advanced through the patient's vasculature until it is positioned near the desired location for the annuloplasty device 200. After positioning the guide catheter, delivery device 212 coupled to the annuloplasty device 200 via coupling mechanism 218 is inserted through the guide catheter to position the annuloplasty device 200 proximate to the mitral annulus. In some embodiments, the delivery device 212 and annuloplasty device 200 are advanced until they are in the coronary sinus and/or the coronary venous vasculature.

The annuloplasty device 200 is advanced to the mitral annulus with the delivery device 212. In some embodiments, the annuloplasty device 200 can be placed proximate to the mitral annulus via the coronary sinus. A fluid can be introduced into shell 202 of the annuloplasty device 200. For instance, the shell 202 of the annuloplasty device 200 can be inflated with a contrast medium or a polymer, which can facilitate the transformation of the annuloplasty device 200 to the deployed configuration. In one or more embodiments, elastic memory of the filaments can cause the annuloplasty device to transform to the deployed configuration. For example, the elastic memory of the filaments can be activated upon introduction of the contrast medium or polymer into the shell, as the same will be known and understood by one of ordinary skill in the art. Fluid can be introduced to the shell 202 of annuloplasty device 200 via lumens 214 and 216, for example. The lumens 214 and 216 are coupled to valves 208 and 210 of the annuloplasty device 200 allowing the contrast medium and the polymer to be transferred from the delivery device 212 to the annuloplasty device 200. In one or more embodiments, lumen 214 can be used to deliver a contrast medium to the annuloplasty device 200 and lumen 216 can be used to deliver a polymer to the annuloplasty device 200. In some embodiments, the contrast medium and the polymer can be delivered to the annuloplasty device via a common lumen. One or more valves can be incorporated to control the filling of the annuloplasty device with fluid, contrast medium, and/or curable polymer. For example, lumen 214 can be used to introduce fluid via valve 208, and lumen 216 can be used to remove fluid from the annuloplasty device via valve 210. A saline and/or contrast medium fluid can be introduced via valve 208 initial deployment of the annuloplasty device, and when satisfactory deployment is achieved, curable polymer is introduced via lumen 214 while the saline and/or contrast medium is removed via lumen 216. An external mechanism (not shown) can control the fluid introduction and removal, maintaining pressures and volumes by opening and/or closing valves to obtain the desired filling of the annuloplasty device and maintain the annuloplasty device in a deployed configuration until the polymer is cured. A lumen can be used to remove the curable polymer prior to curing if a problem is detected.

In one or more embodiments, a contrast medium can aid in viewing the position and shape of the annuloplasty device while deploying the annuloplasty device 200 proximate to the mitral annulus. Also, the filaments 204-1, 204-2, . . . , 204-N can provide radiographic density to aid in viewing the position and the shape of the annuloplasty device 200 during deployment. In some embodiments, radiographic markers can be included on the delivery device 212 and/or the annuloplasty device 200 to aid in viewing the position and the shape of the annuloplasty device during deployment.

In one or more embodiments, the contrast medium is replaced with a curable polymer when the annuloplasty device 200 is positioned at the desired location. For instance, the contrast medium can be removed from the annuloplasty device 200 and a polymer can be introduced into the annuloplasty device 200. The polymer can then be cured to cause the annuloplasty device to take and maintain the deployed configuration at the desired location. The polymer can be cured using thermal exposure, ultraviolet light exposure, electrical exposure, and/or a chemical reaction, among other curing techniques.

In one or more embodiments, annuloplasty device 200 can be inflated via introduction of a curable polymer thereto. The annuloplasty device 200 can then be formed into the deployed configuration of the desired shape at the desired location and the curable polymer can cured to maintain the deployed configuration.

In one or more embodiments, shaping tool 219 can be used to shape the shell and the filaments into the desired shape. Shaping tool 219 can be inserted into the shell 202 via lumen 217 in the annuloplasty device 200. Shaping tool 219 can shape the shell and the filaments into the desired shape of the deployed configuration. A polymer can be introduced into the shell during the shaping process or after the shaping process is complete. Once the shaping tool is removed, the polymer can be cured to cause the annuloplasty device to maintain the desired shape.

In some embodiments, once the annuloplasty device 200 is in the deployed configuration and in the desired location proximate to the mitral annulus, the delivery device 212 can be decoupled from annuloplasty device 200 via the coupling mechanism 208. The delivery device 212 can then be removed from the vasculature.

Figure 3:
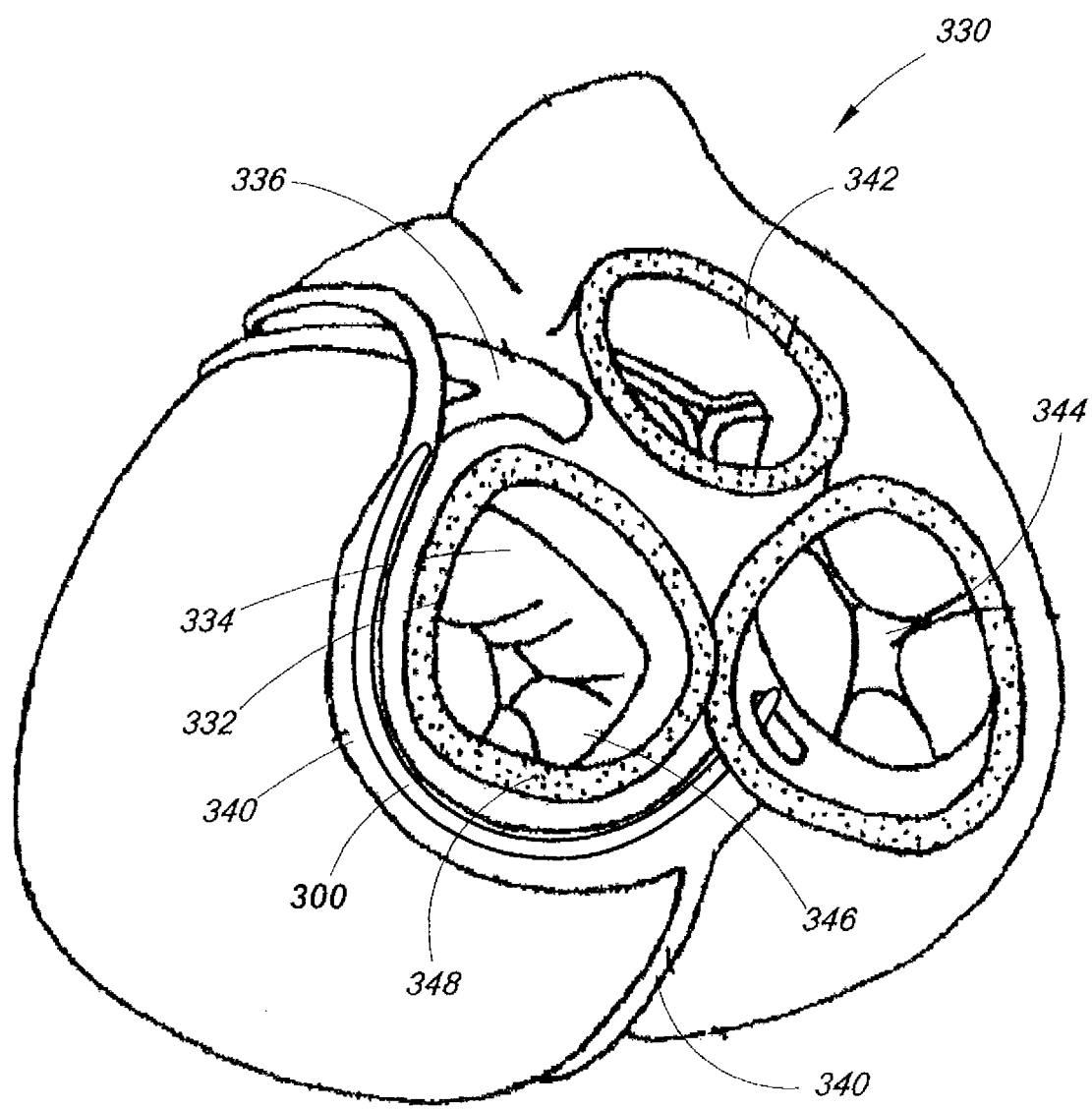
FIG. 3 illustrates an annuloplasty device positioned proximate to a mitral annulus in the coronary venous vasculature in accordance with one or more embodiments of the present disclosure.

FIG. 3 illustrates an annuloplasty device positioned proximate to a mitral annulus in the coronary venous vasculature in accordance with one or more embodiments of the present disclosure. FIG. 3 is a superior view of a heart 330 with the atria removed. The heart 330 comprises several valves including mitral valve 332, the pulmonary valve, aortic valve 342 and tricuspid valve 344. Mitral valve 332 includes anterior cusp 334, posterior cusp 346 and mitral annulus 348. Mitral annulus 348 encircles cusps 334 and 346 and functions to maintain their respective spacing to ensure complete mitral valve closure during left ventricular contractions of the heart 330. In FIG. 3, coronary artery 336 is illustrated at approximately the left main bifurcation to the circumflex and the left anterior descending artery. As illustrated, the venous system includes coronary sinus 340 and partially encircles mitral valve 332 and is adjacent to mitral valve annulus 348. As used herein, coronary sinus refers to the coronary sinus and to the venous system associated with the coronary sinus, including the great cardiac vein.

The coronary sinus 340 is part of the venous system of heart 330 and extends along the atrioventricular (AV) groove between the left atrium and the left ventricle. As such, coronary sinus 340 is essentially within the same plane as mitral valve annulus 348, making coronary sinus 340 available for placement of an annuloplasty device 300 proximate to the mitral annulus 348.

FIG. 3 illustrates one possible embodiment of an annuloplasty device 300 which is deployable through coronary sinus 340 to the mitral annulus 348. Annuloplasty device 300 can be an annuloplasty device such as 100 shown in FIGS. 1A and 1B or 200 shown in FIG. 2. The annuloplasty device 300 can be placed proximate to the mitral annulus in the coronary venous vasculature to provide support for the cusps of the mitral annulus to prevent regurgitation of blood from the left ventricle to the left atrium. The annuloplasty device 300 can be introduced to the mitral annulus through a percutaneous method with minimal invasive techniques. Also, the annuloplasty device 300 can be formed into the desired deployed configuration at the mitral annulus to ensure proper sizing and shape formation. That is, in one or more embodiments, the annuloplasty device 300 can be maintained in an undeployed configuration until it is positioned at the mitral annulus 348. The percutaneous insertion method described can provide various benefits, such as reducing damage to the other parts of the vasculature because the annuloplasty device is moved through the vasculature to the mitral annulus in an elongate introductory configuration that can more easily pass through the vasculature due to its shape (long and tubular) and its flexibility.

Figure 4:
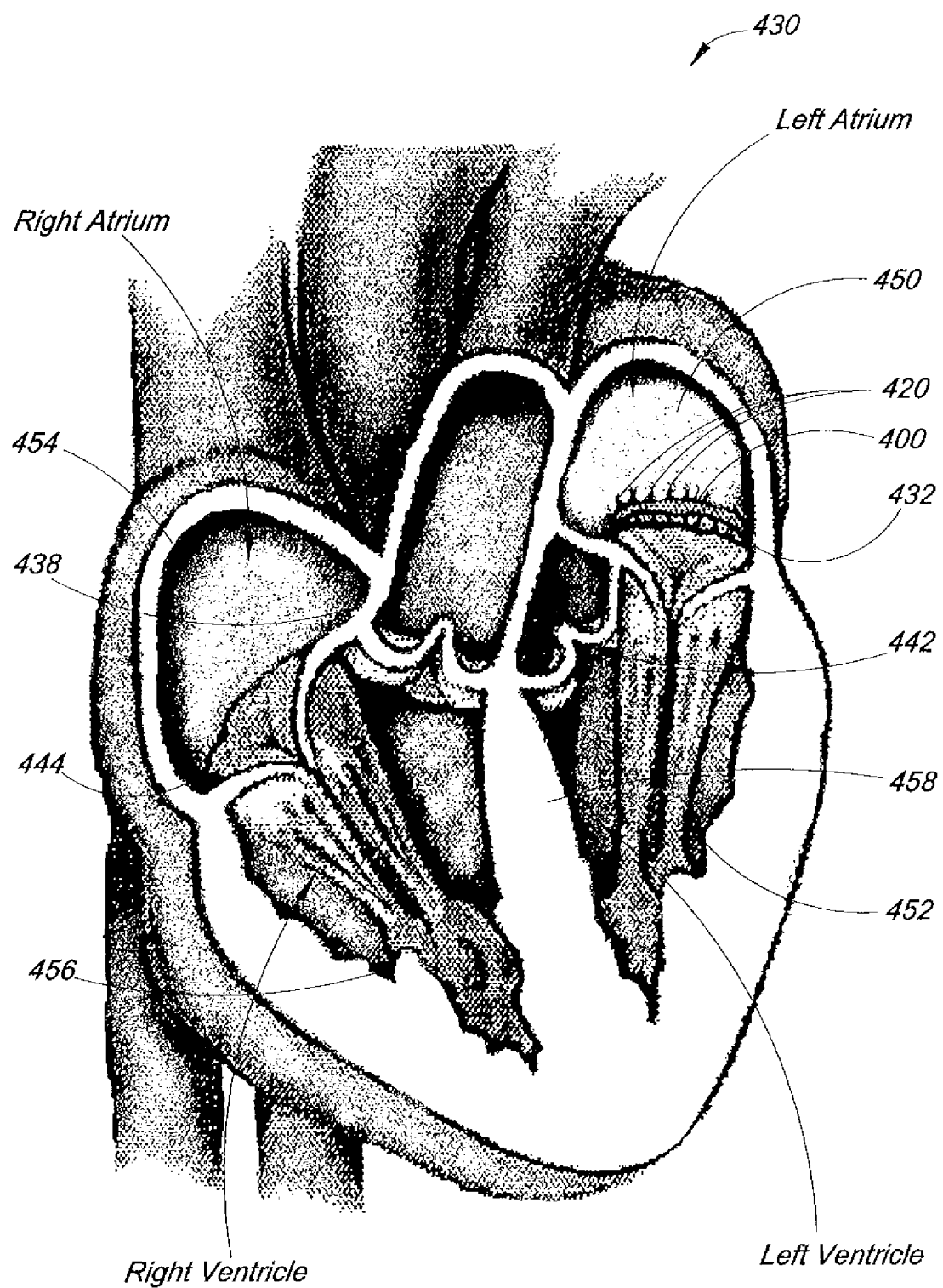
FIG. 4 illustrates an annuloplasty device positioned proximate to a mitral annulus in the left atrium in accordance with one or more embodiments of the present disclosure.

FIG. 4 illustrates an annuloplasty device positioned proximate to a mitral annulus in the left atrium in accordance with one or more embodiments of the present disclosure. The heart comprises the left atrium 450, the left ventricle 452, the right atrium 454, and the right ventricle 456. There are a number of valves controlling the flow of blood within the heart. The valves include the mitral valve 432, the pulmonary valve 438, the aortic valve 442, and the tricuspid valve 444. Mitral valve 432 includes a mitral annulus. The mitral annulus encircles the cusps of the mitral valve and functions to support the mitral valve and to maintain the spacing of the cusps to ensure complete mitral valve closure during left ventricular contractions of the heart 430.

FIG. 4 illustrates one possible embodiment of an annuloplasty device 400 in the left atrium, which is deployable through the coronary sinus to the left atrium. The annuloplasty device 400 can be a device such as device 100 or 200 in FIGS. 1A, 1B, and 2, for example. The annuloplasty device 400 can be placed in the left atrium near the mitral annulus to provide support for the cusps of the mitral annulus and decrease the septal-lateral spacing to obtain desirable cusp apposition and thereby to prevent regurgitation of blood from the left ventricle to the left atrium. The annuloplasty device 400 can be coupled to tissue in the left atrium with attachment mechanisms 420. The annuloplasty device 400 can be introduced to the mitral annulus through a percutaneous method with minimally invasive techniques. Also, the annuloplasty device 400 can be formed into the desired deployed configuration in the left atrium to ensure proper sizing.

The annuloplasty device 400 can be placed proximate to the mitral annulus in the left atrium. Such placement can be beneficial, for instance, when the coronary venous vasculature cannot be used for placement of the annuloplasty device. This allows an annuloplasty to occur using the percutaneous, minimally invasive procedures, device, and systems described herein when other minimally invasive techniques are not available.

Devices, systems, and methods associated with annuloplasty are described herein. In one or more embodiment, an annuloplasty device includes a number of longitudinal filaments moveable between an introductory configuration and a deployed configuration, wherein the number of longitudinal filaments are one or more lengths, and a shell, wherein the shell contains the number of longitudinal filaments and a curable polymer to maintain the annuloplasty device in a deployed configuration.

It will be understood that, although the terms first, second, etc. may be used herein to describe various elements and that these elements should not be limited by these terms. These terms are only used to distinguish one element from another element. Thus, a first element could be termed a second element without departing from the teachings of the present disclosure.

Although specific embodiments have been illustrated and described herein, those of ordinary skill in the art will appreciate that an arrangement calculated to achieve the same results can be substituted for the specific embodiments shown. This disclosure is intended to cover adaptations or variations of various embodiments of the present disclosure.

It is to be understood that the above description has been made in an illustrative fashion, and not a restrictive one. Combination of the above embodiments, and other embodiments not specifically described herein will be apparent to those of skill in the art upon reviewing the above description. The scope of the various embodiments of the present disclosure includes other applications in which the above structures and methods are used. Therefore, the scope of various embodiments of the present disclosure should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the disclosed embodiments of the present disclosure have to use more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. An annuloplasty device, comprising:
a number of longitudinal filaments moveable between an introductory configuration and a deployed configuration, wherein the number of longitudinal filaments are one or more lengths;
a shell, wherein the shell contains the number of longitudinal filaments and a curable polymer to maintain the annuloplasty device in a deployed configuration; and
a number of valves to introduce fluid into the shell to form the shape of the device.

2. The device of claim 1, wherein strengthening additives are included in the polymer.

3. The device of claim 1, wherein attachment mechanisms are included on an outer surface of the shell.

4. The device of claim 1, wherein the number of longitudinal filaments are made of nitinol.

5. The device of claim 1, wherein the number of longitudinal filaments form a pattern within the shell.

6. The device of claim 1, wherein the number of longitudinal filaments and the shell are formed to fit proximate a mitral annulus.

7. The device of claim 1, wherein at least one of the number of longitudinal filaments are coupled to the shell.

8. The device of claim 1, wherein the device includes an opening to introduce a shaping tool to the device.

9. An annuloplasty device delivery system, comprising:
an annuloplasty device, wherein the annuloplasty device includes a number of longitudinal filaments within a shell; and
a delivery device, wherein the delivery device includes a first lumen to introduce a contrast fluid and/or a curable polymer into the annuloplasty device and the delivery device is coupled to the annuloplasty device with a coupling mechanism and configured to position the annuloplasty device proximate to a mitral annulus and transition the annuloplasty device from an introductory configuration to a deployed configuration.

10. The system of claim 9, wherein the delivery device includes a second lumen to remove a saline and/or contrast fluid from the annuloplasty device.

11. The system of claim 9, wherein the coupling mechanism is a detachable coupling mechanism and the delivery device is configured for detachment from the annuloplasty device when the annuloplasty device is placed proximate to the mitral annulus in the deployed configuration.

12. The system of claim 9, wherein the delivery device includes a third lumen to introduce a shaping tool to the annuloplasty device.

13. An annuloplasty device, comprising:
- a number of longitudinal filaments moveable between an introductory configuration and a deployed configuration, wherein the number of longitudinal filaments are one or more lengths;
- a shell, wherein the shell contains the number of longitudinal filaments and a curable polymer to maintain the annuloplasty device in a deployed configuration; and
- an opening to introduce a shaping tool to the device.

* * * * *